United States Patent
Tourrel

(10) Patent No.: US 11,980,754 B2
(45) Date of Patent: May 14, 2024

(54) COCHLEAR IMPLANT DEVICE WITH A FLEXIBLE ELECTRODE ARRAY

(71) Applicant: Oticon Medical A/S, Smørum (DK)

(72) Inventor: Guillaume Tourrel, Vallauris (FR)

(73) Assignee: Oticon Medical A/S, Smørum (DK)

( * ) Notice: Subject to any disclaimer, the term of this patent is extended or adjusted under 35 U.S.C. 154(b) by 265 days.

(21) Appl. No.: 17/508,122

(22) Filed: Oct. 22, 2021

(65) Prior Publication Data

US 2022/0126088 A1    Apr. 28, 2022

(30) Foreign Application Priority Data

Oct. 23, 2020  (EP) .................................. 20203515

(51) Int. Cl.
*A61N 1/05* (2006.01)
*A61N 1/36* (2006.01)
*H04R 25/00* (2006.01)

(52) U.S. Cl.
CPC ........ *A61N 1/0541* (2013.01); *A61N 1/36038* (2017.08); *H04R 25/603* (2019.05); *H04R 2225/57* (2019.05)

(58) Field of Classification Search
CPC .............. A61N 1/0541; A61N 1/36038; A61N 1/36039; H04R 25/60; H04R 2225/05
See application file for complete search history.

(56) References Cited

U.S. PATENT DOCUMENTS

| | | | | |
|---|---|---|---|---|
| 6,428,489 | B1 * | 8/2002 | Jacobsen | A61M 25/09 600/585 |
| 8,283,569 | B2 * | 10/2012 | Johnson | A61N 1/0541 428/458 |
| 9,446,230 | B1 * | 9/2016 | Alshehri | A61N 1/0541 |
| 2011/0295352 | A1 * | 12/2011 | Thenuwara | A61N 1/0541 607/137 |
| 2018/0104473 | A1 * | 4/2018 | Purnell | A61N 1/36038 |
| 2019/0029570 | A1 * | 1/2019 | Stankovic | A61B 5/0084 |

FOREIGN PATENT DOCUMENTS

| | | |
|---|---|---|
| EP | 3 038 702 B1 | 2/2018 |
| WO | WO 01/12115 A1 | 2/2001 |
| WO | WO 2016/085135 A1 | 6/2016 |
| WO | WO 2016/178670 | 11/2016 |

\* cited by examiner

*Primary Examiner* — Allen Porter
*Assistant Examiner* — Christopher J Mutchler
(74) *Attorney, Agent, or Firm* — Birch, Stewart, Kolasch & Birch, LLP

(57) ABSTRACT

The disclosure relates to an electrode array that comprises a first region including a first group of electrodes of a plurality of electrodes and a second region including a second group of electrodes of the plurality of electrodes, where a silicone notch carrier is arranged between the electrodes of the second group, and where each of the silicone notch carrier includes a notch that is formed into the silicone notch carrier, and when the electrode array is straighten each notch has an opening angle and/or a bending radius which varies between the silicone notch carriers.

20 Claims, 10 Drawing Sheets

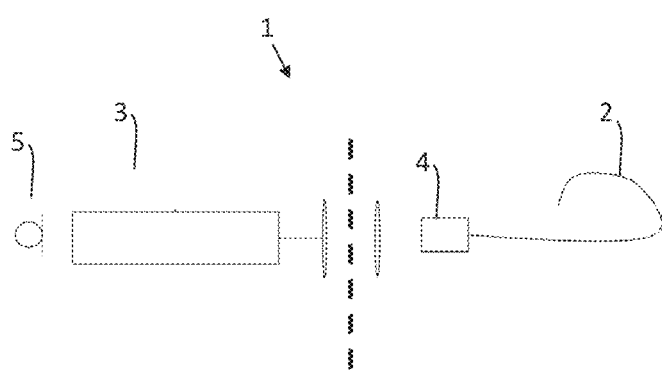
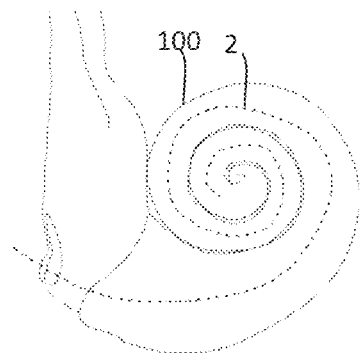
FIG. 1A
FIG. 1B

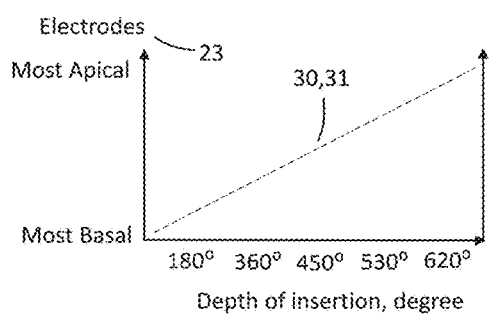
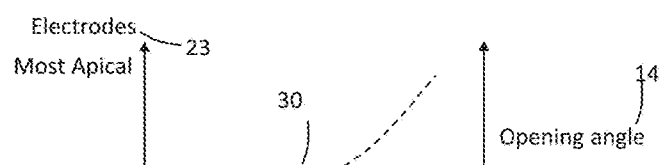
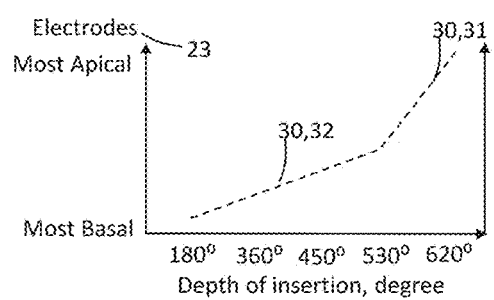
FIG. 3A
FIG. 3B
FIG. 3C

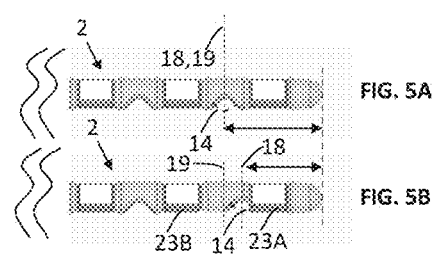
FIG. 5A
FIG. 5B
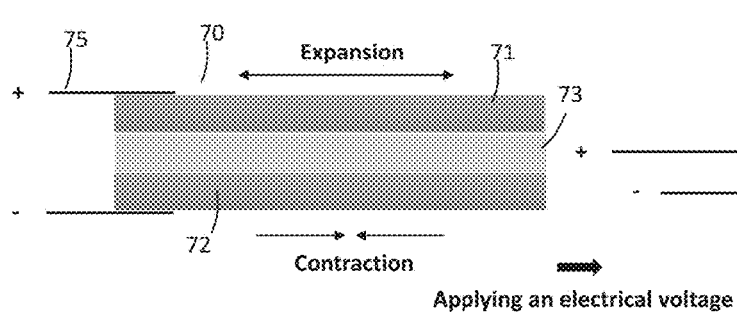
Applying an electrical voltage
FIG. 6A
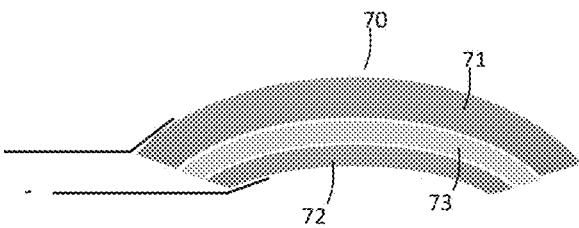
FIG. 6B

COCHLEAR IMPLANT DEVICE WITH A FLEXIBLE ELECTRODE ARRAY

FIELD

The present disclosure relates to a cochlear implant device. More particularly, the disclosure relates to an electrode array having different regions where in one of the regions the flexibility of the electrode array varies.

BACKGROUND

The present disclosure relates to a cochlear implant device used to electrically stimulate the auditory nerve fibers of a cochlea of a recipient. More particularly, the present disclosure relates to an implantable electrode array for use with a cochlear stimulator. Such implantable electrode array is designed to Place electrode contacts of the electrode array generally along one side of the array so that when the array is implanted, e.g., in the cochlea, the side of the array whereon the electrode contacts are located can be positioned in close proximity to the cells that are to be stimulated, thereby allowing such cells to be stimulated with minimal power consumption.

The hearing loss phenomenon, which may be due to many different causes, is generally of two types: conductive and sensorineural. Of these, conductive hearing loss occurs where the normal mechanical pathways for sound to reach the hair cells in the cochlea are impeded, for example, by damage to the ossicles. Conductive hearing loss may often be helped h use of conventional hearing aids, which amplify sound so that acoustic information does reach the cochlea and the hair cells. Some types of conductive hearing loss are also amenable to alleviation by surgical procedures.

In many people who are profoundly deaf, however, the reason for their deafness is sensorineural hearing loss. This type of hearing loss is due to the absence or the destruction of the hair cells in the cochlea which are needed to transduce acoustic signals into auditory nerve impulses. These people are unable to derive any benefit from conventional hearing aid systems, no matter how loud the acoustic stimulus is made, because their mechanisms for transducing sound energy into auditory nerve impulses have been damaged. Thus, in the absence of properly functioning hair cells, there is no way auditory nerve impulses can be generated directly from sound To overcome sensorineural deafness, there have been developed numerous cochlear implant devices which seek to bypass the hair cells in the cochlea (the hair cells are located in the vicinity of the radially outer wall of the cochlea) by presenting electrical stimulation to the auditory nerve fibers directly, leading to the perception of sound in the brain and at least partial restoration of hearing function. The common denominator in most of these cochlear devices has been the implantation into the cochlea of electrodes which are responsive to a suitable external source of electrical stimuli and which are intended to transmit those stimuli to the ganglion cells and thereby to the auditory nerve fibers.

A cochlear implant device operates by direct electrical stimulation of the auditory nerve cells, bypassing the defective cochlear hair cells that normally transduce acoustic energy into electrical activity in such nerve cells. In addition to stimulating the nerve cells, the electronic circuitry and the electrode array of the cochlear implant device the function of the separating the acoustic signal into a number of parallel channels of information, each representing the intensity of a narrow band of frequencies within the acoustic spectrum.

Ideally, each channel of information would be conveyed selectively to the subset of auditory nerve cells that normally transmitted information about that frequency band to the brain. Those nerve cells are arranged in an orderly tonotopic sequence, from high frequencies at the basal end of the cochlear spiral to progressively lower frequencies towards the apex. In practice, this goal tends to be difficult to realize because of the anatomy of the cochlea.

A consensus has generally emerged that the Scala tympani, one of the three parallel ducts that, in parallel, make up the spiral-shaped cochlea, provides the best location for implantation of an electrode array used with a cochlear implant device. The electrode array to be implanted in this site typically consists of a thin, elongated, flexible carrier containing several longitudinally disposed and separately connected stimulating electrode contacts.

During the implantation of the electrode array, trauma may be induced to the basilar membrane provided by contact with the electrode array. For reducing the induced trauma, a higher flexible electrode array is needed. EP3038702B1 solves the problem by applying cutouts into sections of the electrode array for improving the deformation of the electrode array. The shape of cutouts is the same providing a uniformly deformation profile along the section of the electrode array which includes the cutouts.

Along the cochlea from the basal part to the apical part, the curvature radius varies and becomes smaller when approaching, the apical part, and therefore, there is a Peed of having an electrode array where the flexibility along the electrode array varies, i.e. that the deformation profile along a section of the electrode array should be non-uniformly.

SUMMARY

An aspect of the disclosure is to provide a flexible electrode array with an improved flexibility in relation to the curvature radius of a cochlea.

The aspect of the disclosure is achieved by a cochlear implant device which May comprise an implantable receiving unit configured to receive a plurality of electric stimulation pulses, and an electrode array including a plurality of electrodes configured to stimulate auditory nerve fibers of a cochlea of a recipient based on the plurality of electric stimulation pulses.

The electrode array may comprise a first region including a first group of electrodes of the plurality of electrodes and a second region including a second group of electrodes of the plurality of electrodes, where a silicone notch carrier is arranged between the electrodes of the second group, and where each of the silicone notch carrier includes a notch which is formed into the silicone notch carrier, and when the electrode array is straighten each notch has an opening angle and/or a bending radius which varies between the silicone notch carriers.

The electrode array may comprise a first region including a first group of electrodes of the plurality of electrodes, where a silicone carrier is arranged between the electrodes of the first group, and a second region including a second group of electrodes of the plurality of electrodes, where a silicone notch carrier is arranged between the electrodes of the second group, and where each ref the silicone notch carrier includes a notch which is formed into the silicone notch carrier, and when the electrode array is straighten each notch has an opening angle and/or a bending radius which varies bet the silicone notch carriers according to a dimension profile.

The curvature radius of the cochlea varies along a length of the cochlea and becomes smaller from a basal part to an apical part of the cochlea, and thereby, for minimizing trauma induced to the cochlea during insertion of the electrode array, it is important that the variable flexibility of the electrode array at least varies along a longitudinal length of the electrode array. This is obtained by applying the notch in the silicone notch carriers, where for example the opening angle increases along the second region of the electrode array towards the most apical electrode of the second group of electrodes. Furthermore, this is also obtained by applying the notch in the silicon notch carriers, where for example a bending radius decreases along the second region of the electrode array towards the most apical electrode of the second group of electrodes.

The size of the opening angle and the bending radius of the at least two or more notches may be determined based on a 3D image of a recipient's cochlea.

The size of the opening angle and the bending radius of the at least two or more notches may be pre-fitted to a recipient via a 3D image of the recipient's cochlea or via a cochlea model which is determined based on other persons.

When the electrode array is inserted into the cochlea, the second region is arranged closer to the apical part of the cochlea than the first region. The electrode array is more flexible in the second region than in the first region.

The first region including the first group of electrodes of the plurality of electrodes may further include a silicone carrier arranged between the electrodes of the first group. Thereby, the electrode array becomes slightly flexible within the first region, but, the second region is still more flexible than the first region. Thus, by applying the silicone carrier between the electrodes within the first group, the electrode array obtains a flexibility which is suitable for minimizing trauma induced to the cochlea and for not bending the electrode array in the first region during insertion of the electrode array.

The opening angle and/or the bending radius of the at least two or more notches in the second region vanes between the notches of the silicone notch carriers according to a dimension profile. The dimension profile may include at least one of following profiles or a combination of following profiles:

the opening angle decreases from a most apical electrode of the second group of electrodes to a first electrode of the second group of electrodes;

the opening angle decreases from a most apical electrode of the second group of electrodes to a most basal electrode of the second group of electrodes;

the bending radius increases from a most apical electrode of the second group of electrodes to a first electrode of the second group of electrodes; and/or the bending radius increases from a most apical electrode of the second group of electrodes to a most basal electrode of the second group of electrodes.

By being able to apply different variation of the opening angle and/or the bending radius results in an Unproved Way of adapting the flexibility of the electrode array to the shape of the cochlear or to the curvature radius of the cochlear.

The opening angle may decrease from a most apical electrode of the second group of electrodes to a first electrode of the second group of electrodes, and the opening angle may decrease from a second electrode of the second group of electrodes to a most basal electrode of the second group of electrodes.

The opening angle may decrease from a most apical electrode of the second group of electrodes to a first electrode of the second group of electrodes, and the opening angle may be constant from the first electrode to a second electrode of the second group of electrodes, and the opening angle may decrease from the second electrode of the second group of electrodes to a most basal electrode of the second group of electrodes.

The opening allele may decrease from a most apical electrode of the second group of electrodes to a first electrode of the second group of electrodes, and the opening angle may be constant from the first electrode to a most basal electrode of the second group of electrodes.

Each of the at least two or More notches are formed into a first surface of the silicone notch carrier, where the first surface is directed towards the spiral ganglion of the cochlea when the electrode array is inserted into the cochlea. Thereby, an improved stimulation of the auditory nerve fibers is obtained while having the flexibility in the second region.

For improving the flexibility of an apical end of the electrode array, it is an advantage to arrange a center of the opening angle asymmetrical between the most apical electrode of the second region and a neighboring electrode to the most apical electrode. The neighboring electrode is part of the second group of electrodes. The center of the opening angle of at least a silicone notch carrier between a most apical electrode of the second group of electrodes and a first electrode of second group of electrodes is asymmetrical arranged. For the remaining silicone notch carriers, a center of the opening angle may be symmetrical arranged. Therefore, the center of the opening angle may be symmetrical or asymmetrical arranged in the silicone notch carrier.

The at least two or more notches shape an open volume which does not include the material of the silicone notch carrier.

The improved flexibility of the electrode array may be exploit further to obtain an electrode array where the curvature along the electrode array may be controlled during insertion of the electrode array into the cochlea. Therefore, the silicone notch carriers may include a curvature controller, or a curvature controller may be applied onto the silicone notch carriers, and wherein the curvature controller is configured to control the size of the opening angle and/or the bending radius of the notch. The curvature controller may be in one piece extending across the silicone notch carriers, and where each electrode of the second group of electrodes is connected to the curvature controller.

The cochlear implant device may comprise an implantable receiving unit configured to receive a plurality of electric stimulation pulses, and an electrode array including a plurality of electrodes configured to stimulate auditory nerve fibers of a cochlea of a recipient based on the plurality of electric stimulation pulses. The electrode array may comprise a first region including a first group of electrodes of the plurality of electrodes, and a second region including a second group of electrodes of the plurality of electrodes, where a silicone notch carrier is arranged between the electrodes of the second group, and where each of the silicone notch carrier includes a notch which is formed into the silicone notch carrier. The one or more of the silicone notch carriers may include the curvature controller configured to control the sin of the opening angle and/or the bending radius of the notch.

The curvature controller may include a micro transducer which is connected to at least one electrode of the second group of electrodes, and wherein the size of the opening angle of a notch is determined by an electrical signal level transmitted by the at least one electrode.

The curvature controller may include a micro transducer which is connected to at least one wire of the electrode array, and wherein the size of the opening angle of a notch is determined by an electrical signal level transmitted by the at least one wire. The wire is no used for providing electrical stimulation of auditory nerve fibers.

During insertion of the electrode array the electrode array may be connected to an external controller or the implantable receiving unit which is configured to apply the electrical signals to the curvature controller for adjusting the opening angle and/or the bending radius of the electrode array. Thereby, it is possible to adjust the curvature and/or the bending radius at different locations along the electrode array. By having the possibility of adjusting the opening angle and/or the bending radius will result in a reduced risk of inducing trauma to the cochlear caused by the electrode array.

The micro transducer is a small active element from which it is possible to control the curvature of the electrode by applying an electric voltage to two input terminals of the micro transducer. The electric voltage may be applied by the implantable receiving unit and/or by an external unit via the transcutaneous link or via a wired connection. The electric voltage may be applied by the electrodes of the plurality of electrodes. The materials that are used in a micro-transducer are called Electro Active Polymer (EAP) and can be sort out into two main categories; the electronic-EAP (eEAP) and the ionic-EAP (iEAP). In eEAP the actions are based on electrons transportation, while in iEAP is based on ions. The main principle of EAP is the material volume change when applying a voltage to the input terminals. The micro-transducer is generally composed of multiple layers of EAP material including, a first layer that expands during activation and at least a second layer that shrinks during activation, leading to a bending of the structure.

The micro transducer may be integrated into the electrode array, and More specifically, into the silicone notch carriers, where each of the micro transducer is controlled separately. In this example, each of the micro transducer receives independently an electric voltage from the implantable receiving unit and/or an external unit via the transcutaneous link or via a wired connection. Or, each of the micro transducer may receive independently an electric voltage from each of the plurality of electrodes.

Each of the micro transducers may separately be connected to a control unit within the implantable receiving unit or the external unit, where the control unit is configured to control the electrical voltage to each of the micro transducer. More specifically, the micro transducers are connected to the control unit via a parallel wire lead. The control unit is configured to activate the micro transducers according to the insertion depth of the electrode array for the purpose of bending the electrode array in accordance to the shape and curvature of the cochlea. During the insertion of the electrode array, the most apical micro transducer will be activated progressively, followed by the more basal micro transducers, to finally mimic the cochlea shape. The expected benefit is to reduce drastically the insertion forces needed for introducing the electrode array into the cochlea, and consequently, for reducing the risk of applying trauma to the cochlea.

The micro transducer may be integrated such that more than one silicon notch carrier shares the same micro transducer. In this example, less additional wires are needed.

Before and during insertion of the electrode array a temporary carrier may be added to an outer surface or the electrode or to an inner guiding section of the electrode array. The temporary carrier may be glued onto the outer surface, and the glued is dissolved by the perilymph and the temporary carrier is released from the electrode array. Thereby, the carrier can be pulled out of the cochlea while keeping the electrode array in place.

The glue may be a soluble biocompatible material, a gelatin or polysaccharide-based biomaterial.

The temporary carrier may include one or more micro transducers. The electrical voltage is controlled by the implantable receiving unit or the external unit connected to the implantable receiving unit via the transcutaneous link or via a wired connection.

When the electrode array is arranged correctly in the cochlea of the recipient, the temporary carrier is pulled out of the inner guiding section.

The carrier may be temporarily attached to the inner guiding section via a fixing mean. The fixing mean may be arranged at the most basal end of the electrode array.

The external unit may be a computer or a sound processor which is configured to communicate with the implantable receiving unit via the transcutaneous link. The sound processor is configured to be arranged on or at the head of the recipient.

BRIEF DESCRIPTION OF DRAWINGS

The aspects of the disclosure may be best understood from the following detailed description taken in conjunction with the accompanying figures. The figures are schematic and simplified for clarity, and they just show details to improve the understanding of the claims, while other details are left out. Throughout, the same reference numerals are used for identical or corresponding parts. The individual features of each aspect may each be combined with any or all features of the other aspects. These and other aspects, features and/or technical effect will be apparent from and elucidated with reference to the illustrations described hereinafter in which:

FIGS. 1A and 1B illustrate an example of a cochlear implant device

FIGS. 3A to 3C illustrate different examples of a dimension profile;

FIGS. 5A and 5B illustrate examples of a silicone notch carrier;

FIGS. 6A and 6B illustrate examples of a curvature controller;

DETAILED DESCRIPTION

Figure 2A:
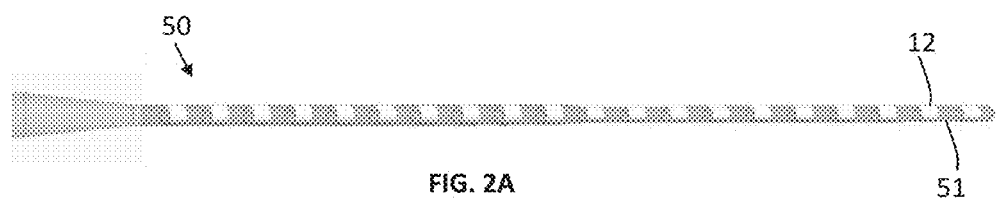
FIGS. 2A to 2C illustrate different example of an electrode array.

The detailed description set forth below in connection with the appended drawings is intended as a description of various configurations. The detailed description includes specific details for the purpose of providing a thorough understanding of various concepts. However, it will be apparent to those skilled in the art that these concepts may be practiced Without these specific details. Several aspects of the apparatus and methods are described by various blocks, functional units, modules components, circuits, steps, processes, algorithms, etc. (collectively referred to as "elements"). Depending upon particular application, design constraints or other reasons, these elements may be implemented using electronic hardware, computer program, or any combination thereof.

A hearing aid may be or include a hearing aid that is adapted to improve or augment the tearing capability of a user by receiving an acoustic signal froth a user's surroundings, generating a corresponding audio signal, possibly modifying the audio signal and providing the possibly modified audio signal as an audible signal to at least one of the user's ears. 'Improving or augmenting the hearing capability of a user' include compensating for an individual s specific hearing loss. The "hearing aid" mays further refer to a device such as a hearable, an earphone or a headset adapted to receive audio signal electronically, possibly modifying the audio signal and providing the possibly r modified audio signals as an audible signal to at least one of the user's ears. Such audible signals may be provided in the form of an acoustic signal radiated into the user's outer ear, or an acoustic signal transferred as mechanical vibrations to the user's inner ears through bone structure of the user's head and/or through parts of the middle ear of the user or electric signals transferred directly or indirectly to the cochlear nerve and/or to the auditory cortex of the user.

The hearing id is adapted to be worn in any known way. This may include i) arranging a unit of the hearing aid behind the ear with a tube leading air-borne acoustic signals into the ear canal or with a receiver/loudspeaker arranged close to or in the ear canal and connected by conductive wires (or wirelessly) to the unit behind the ear, such as in a Behind-the-Ear type hearing aid, and/or ii) arranging the hearing aid entirely or partly in the pinna and/or in the ear canal of the user such as in an In-the-Ear type heating aid or In-the-Canal/Completely-in-Canal type hearing aid, or iii) arranging a unit of the hearing aid attached to a fixture implanted into the skull bone such as in a Bone Anchored Hearing Aid or a Cochlear implant, or iv) arranging a unit of the hearing aid as an entirely or partly implanted unit such as in a Bone Anchored Hearing Aid or a Cochlear implant system. The hearing aid may be implemented in one single unit (housing) or in several units individually connected to each other.

A "hearing system" refers to a system comprising one or two hearing aids, and a "binaural hearing system" refers to a system comprising two hearing aids where the devices are adapted to cooperatively provide audible signals to both user's ears. The hearing system or binaural hearing system may further include one or more auxiliary device(s) that communicates with at least one hearing aid, the auxiliary device affecting the operation of the hearing aids and/or benefiting from the functioning of the hearing aids. A wired or wireless communication link between the at least one hearing aid and the auxiliary device is established that allows for exchanging information (e.g. control and status signals, possibly audio signals) between the at least one hearing aid and the auxiliary device Such auxiliary devices may include at least one of a remote control, a remote microphone, an audio gateway device, a wireless communication device, e.g. a mobile phone (such as a smartphone) or a tablet or another device, e.g. comprising a graphical interface, a public-address system, a car audio system or a music player, or a combination thereof. The audio gateway may be adapted to receive a multitude of audio signals such as from an entertainment device like a TV or a music player, a telephone apparatus like a mobile telephone or a computer, e.g. a PC. The auxiliary device may further be adapted to (e.g. allow a user to) select and/or combine an appropriate one of the received audio signals (or combination of signals) for transmission to the at least one hearing aid. The remote control is adapted to control functionality and/or operation of the at least one hearing aid. The function of the remote control may be implemented in a smartphone or other (e.g. portable) electronic device, the smartphone/electronic device possibly riming an application (APP) that controls functionality of the at least one hearing aid.

In general, a hearing aid includes a receiving unit such as a microphone for receiving an acoustic signal from a user's surroundings and providing a corresponding input audio signal, and/or ii) a receiving unit for electronically receiving, an input audio signal. The hearing aid further includes a signal processing unit for processing the input audio signal and an output unit for providing an audible signal to the user in dependence on the processed audio signal.

The receiving unit may include multiple input microphones, e.g. for providing direction-dependent audio signal processing. Such directional microphone system is adapted to (relatively) enhance a target acoustic source among a multitude of acoustic sources in the user's environment and/or to attenuate other sources (e.g. noise). In one aspect, the directional system is adapted to detect (such as adaptively detect) from which direction a part of the microphone signal originates. This may be achieved by using conventionally known methods. The signal processing unit may include an amplifier that is adapted to apply a frequency dependent gain to the input audio signal. The signal processing unit May further be adapted to provide other relevant functionality such as compression, noise reduction, etc. The output unit may include an output transducer such as a loudspeaker/receiver for providing an air-borne acoustic signal transcutaneous or percutaneously to the skull bone or a vibrator for providing a structure-borne or liquid-borne acoustic signal. In some hearing aids, the output unit may include one or more output electrodes for providing the electric signals such as in a Cochlear Implant.

A Cochlear Implant typically includes i) an external part for picking up and processing sound from the environment, and for determining sequences of pulses for stimulation of the electrodes in dependence on the current input sound, ii) a (typically wireless, e.g. inductive) communication link for simultaneously transmitting information about the stimulation sequences and for transferring energy to iii) an implanted part allowing the stimulation to be generated and applied to a number of electrodes, which are implantable in different locations of the cochlea allowing a stimulation of different frequencies of the audible range. Such systems are e.g. described in U.S. Pat. No. 4,207,441 and in U.S. Pat. No. 4,532,930.

In an aspect, the hearing aid comprises multi-electrode array e.g. in the form of a carrier comprising a multitude of electrodes adapted for being in the cochlea in proximity of an auditory nerve of the user. The carrier is preferably made of a flexible material to allow proper positioning of the electrodes in the cochlea such that the electrodes may be inserted in cochlea of a recipient. Preferably, the individual electrodes are spatially distributed along the length of the carrier to provide a corresponding spatial distribution along the cochlear nerve in cochlea when the carrier is inserted in cochlea.

FIGS. 1A and 1B illustrate an example of a cochlear implant device 1 that optionally includes an external unit 3 and an implantable receiving unit 4 that is implanted between the skull and the skin of the recipient. The implantable receiving unit is configured to receive a plurality of electric stimulation pulses via a transcutaneous link from an external unit 3. The external unit 3 may be arranged on or at the head of the user. The external unit may include a microphone 5 configured to receive an acoustical signal, and the external unit 3 is configured to determine the plurality of electric stimulation pulses based on the acoustical signal. The implantable receiving unit 4 is connected to an electrode array 2 that includes a plurality of electrodes configured to stimulate auditory nerve fibers of a cochlea of the recipient based on the electrical stimulation pulses. FIG. 1B illustrate the electrode array 2 being inserted into the cochlea 100 of the recipient.

Figure 2B:
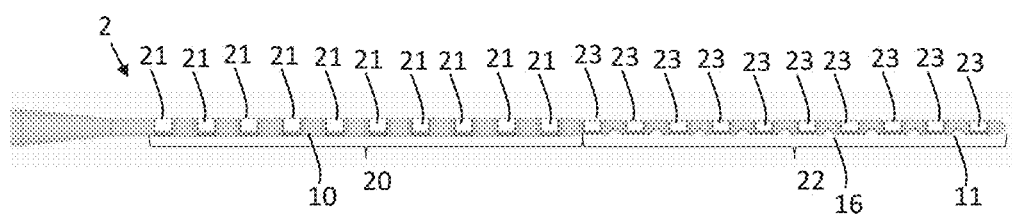
Figure 2C:
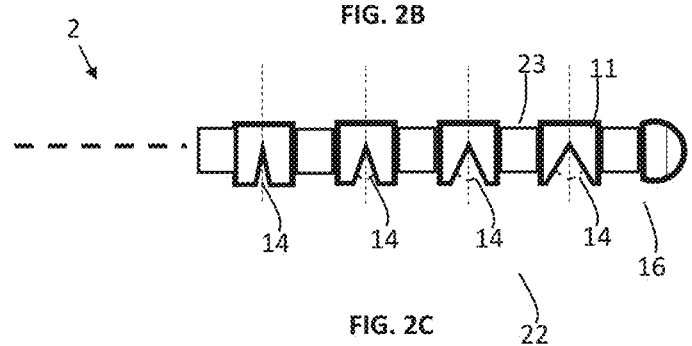

FIG. 2A illustrate a known electrode array including a plurality of electrodes 12 where a flexible carrier 51 is arranged between each of the plurality of electrodes 12 for enhancing the flexibility of the electrode array 2. FIG. 2B illustrate the electrode array 2 including a first region 20 which includes a first group of electrodes 21 of the plurality of electrodes 12. In this specific example, a silicone carrier 10 is arranged between each of the electrodes 21 of the first group 20, however, in another example where a less flexible electrode array is needed in the first region, a none-silicone carrier may be arranged between the electrodes 21 of the first group 20. The electrode array 2 includes a second region 22 that comprises a second group of electrodes 23 of the plurality of electrodes 12, where a silicone notch carrier 11 is arranged between the electrodes of the second group 22. FIG. 2C illustrates that when the electrode array is straighten each notch in the silicone notch carrier has an opening angle 14 that varies between the carriers 11.

The opening angle of the at least two or more notches 11 in the second region may vary between the notches of the silicon notch carriers according to a dimension profile 30.

Each of the at least two or more notches are formed into a first surface 16 of the silicone notch carrier 11, where the first surface 16 is directed towards a spiral ganglion of the cochlea when the electrode array 2 is inserted into the cochlea. By applying the notches into the first surface 16 results in a bending of the electrode array 2 in the direction of the curvature of the cochlea.

The notches shape an open volume which does not include the material of the silicone notch carrier.

FIGS. 3A to 3C illustrate different examples of the dimension profile 30. On the x axis the insertion angle is mentioned in relation to the electrodes 23 of the electrode array 2. Furthermore, an opening angle 14 is defined for each of the silicone notch carrier 11 in relation to the electrode(s) 23 arranged next to the silicone notch carrier 11 and the expected insertion depth of these electrode(s) 23 in the cochlea of the recipient. In FIG. 3A, the dimension profile 30 defines a decrease in the opening angle 14 from the most apical electrode 23 to the most basal electrode 23 of the second region 22. The decrease in the opening angle 14 between the silicon notch carriers 11 may be defined by a first slope coefficient 31. In FIG. 3B, the dimension profile 30 defines a decrease in the opening angle 14 from the most apical electrode 23 to the most basal electrode 23 of the second region. The decrease in the opening angle 14 between the silicon notch carriers 11 may be defined by a first slope coefficient 31 and at least a second slope coefficient 32. The first slope coefficient 31 and/or the second slope coefficient 32 may be determined by the shape of a cochlea. In FIG. 3C, the dimension profile is determined by the shape of a cochlea. The cochlea may either be the cochlea of the recipient of the cochlear implant device or a model of a cochlea determined based on one or more other persons.

In other examples the dimension profile includes at least one of following profiles or a combination of following dimension profiles:

the opening angle 14 decreases from a most apical electrode of the second group of electrodes to a first electrode of the second group of electrodes;

the opening angle 14 decreases from a most apical electrode of the second group of electrodes to a most basal electrode of the second group of electrodes;

the bending radius increases from a most apical electrode of the second group of electrodes to a first electrode of the second group of electrodes; and/or the bending radius increases from a most apical electrode of the second group of electrodes to a most basal electrode of the second group of electrodes.

Figure 4:
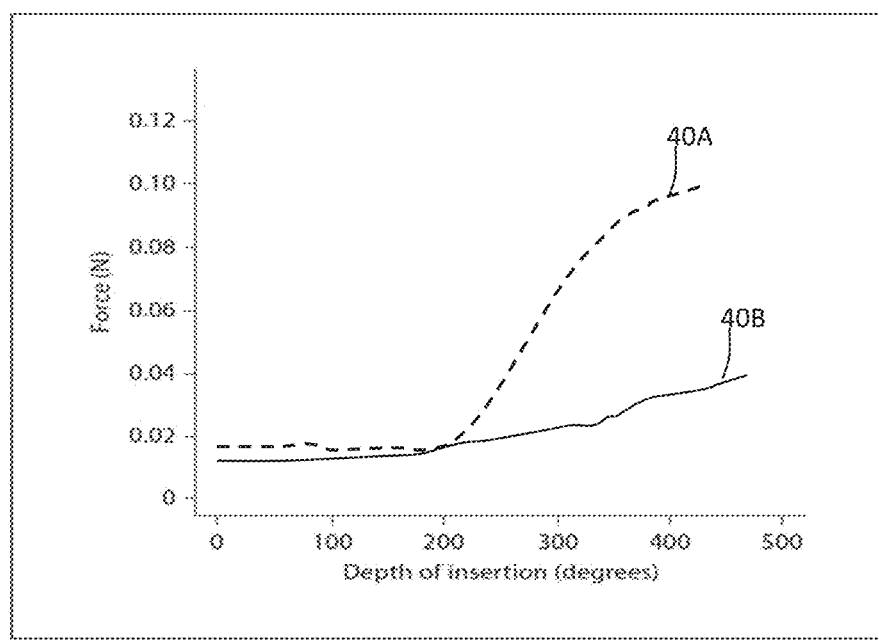
FIG. 4 illustrates an example of insertion force applied to the electrode array.

FIG. 4 illustrates an example of the force needed for inserting the electrode array 2 into a cochlea. The force for inserting the electrode army increases as the insertion depth of the electrode array 2 increases. Curve 40A illustrates the change in the insertion farce as the insertion depth increases for the electrode array 50 that comprises flexible carriers 51. Curve 40B illustrates the change in the insertion force as the insertion depth increases for the electrode array 2 that comprises silicone notch carriers 11. The average insertion force is lower for the electrode array 2 with the silicone notch carriers 11 in comparison to the electrode array without the silicone notch carriers 11.

FIGS. 5A and 5B illustrates examples on how a center 18 of the opening angle 14 is arranged in the silicone notch carrier 11 according a center 19 of the silicone notch carrier 11. FIG. 5A illustrates an example where the center 18 of opening angle 14 is arranged symmetrical according to the center 19 of the silicone notch carrier 11. FIG. 5B illustrates an example where the center 18 of the opening angle 14 is arranged asymmetrical according to the center 19 of the silicate notch carrier 11. More specifically, FIG. 5B illustrates an example where the center 18 of the opening angle 14 of at least a silicone notch carrier 11 between a most apical electrode 23A of the second group 23 of electrodes and a first electrode 23B of the second group 23 of electrodes is asymmetrical arranged.

For reducing even more, the risk of inducing trauma to the cochlea, due to collision between the electrode array and the cochlea, an electrode array 2 with a curvature controller is needed. Via the curvature controller it is possible to adapt the bending of the electrode array 2 to the shape of the cochlea while inserting the electrode array 2 into the cochlea. The curvature controller is configured to control the site of the opening angle 14 and/or the bending radius of the notch in the silicone notch carrier 2 based on an electrical voltage. FIGS. 6A and 6B illustrates an example of the curvature controller 70, which in this example includes a micro transducer 70. In this example, the micro-transducer 70 is composed of multiple layers of EAP material including a first layer 71 that expands during activation and at least a second layer 72 that shrinks during activation, leading to a bending of the structure. An electrically conductive layer 73 is introduced between the first layer 71 and the second layer 72. The activation of the layers (71, 72) is provided via input terminals 75 that are connected v is the electrodes 73 or separate wires to the implantable receiving, unit 4 and/or the external unit. FIG. 6A illustrates an example where no voltage is applied to the input terminals 75. FIG. 6B illustrates an example where an electrical voltage is applied to the input terminals 75 resulting in a bending of the micro transducer 70.

Figure 7A:
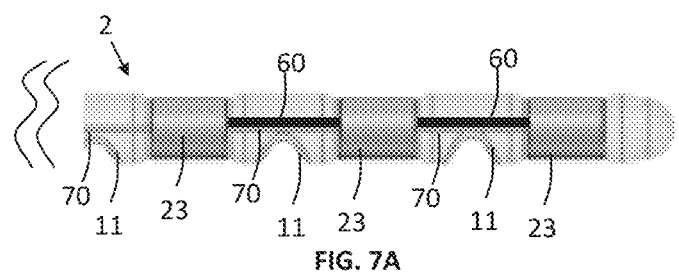
FIGS. 7A and 7B illustrate examples of a curvature controller.
Figure 7B:
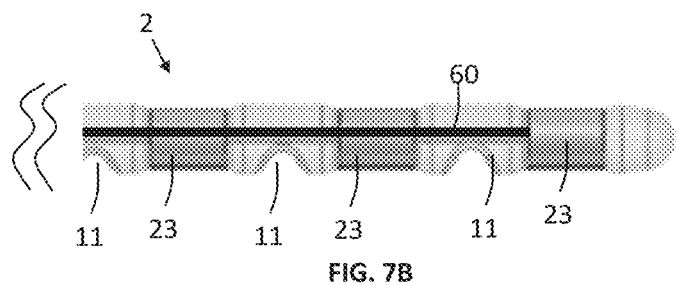

FIGS. 7A and 7B illustrate different examples of implementation of the curvature controller 60. FIG. 7A illustrates an example where each silicon notch carrier comprises a curvature controller 60 applied on to a wire 70 connecting an electrode to the implantable receiving unit 4. The curvature controller comprises input terminals that are electrical connected to the implantable receiving unit 4 or an external unit via the electrode 23 or a separate wire. The advantage of utilizing the electrode 23 for providing the electrical voltage to the input terminals 75 is that no further wires are applied into the electrode array 2. FIG. 7B illustrates an example where the silicon notch carriers 11 share a single micro transducer 60, and in this example, the curvature controller 60 is configured to bend differently along the transducer and within sections of the transducer 60 that are defined by the silicon notch carriers.

Figure 8A:
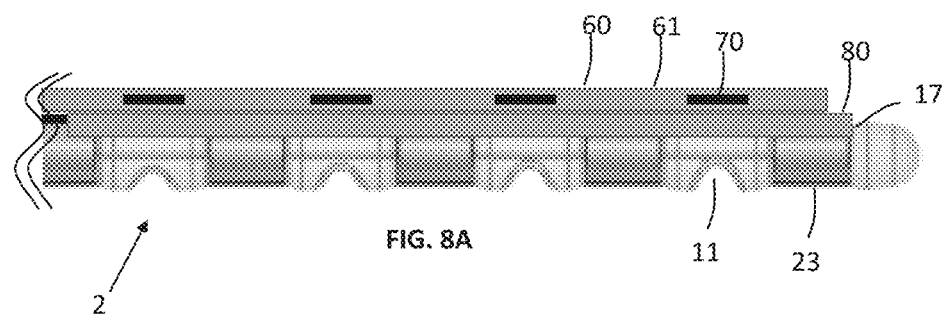
FIGS. 8A and 8B illustrate examples of a curvature controller.
Figure 8B:
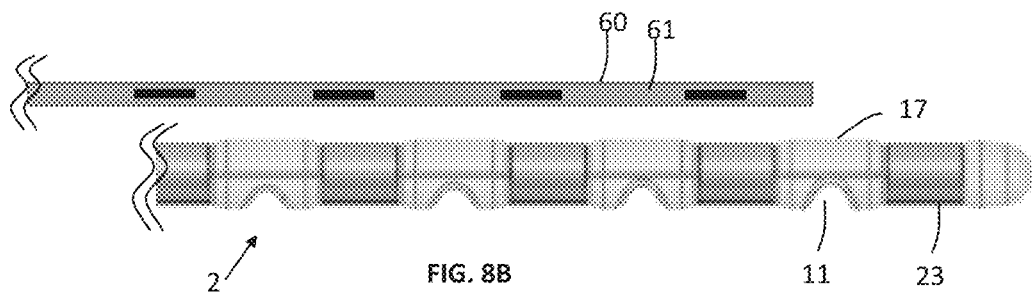

FIGS. 8A and 8B illustrate different examples of implementation of the curvature controller 60 which comprises multiple of micro transducers 70 that are connected via wires to an external unit. FIG. 8A illustrates the curvature controller 60 being applied onto a second surface 17 of the electrode array be second surface 17 is an outer surface of the electrode array 2. The curvature controller 60 includes a temporary carrier that comprises, the micro transducers 70, and the temporary carrier is glued 80 onto the second surface 17. FIG. 8B illustrates an example where the glue 80 is dissolved and the carrier 61 can be released from the electrode array 2. The glue 80 may be a soluble biocompatible material, a gelatin or polysaccharide-based biomaterial.

Figure 9A:
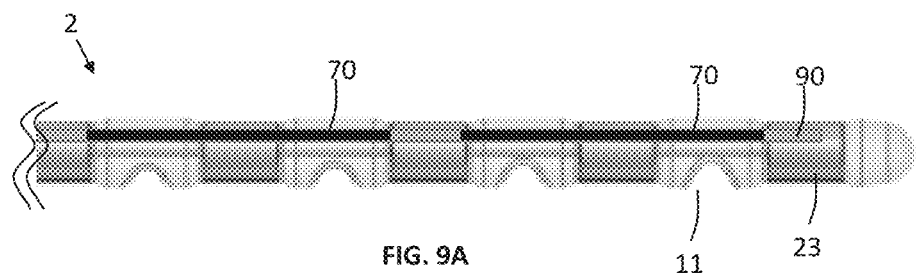
FIGS. 9A and 9B illustrate examples of a curvature controller.
Figure 9B:
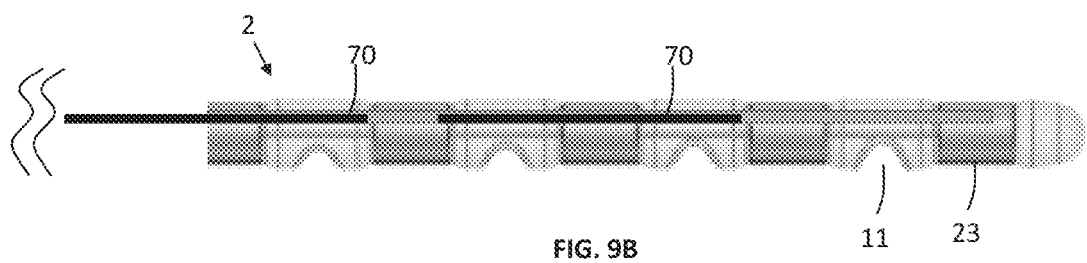

FIGS. 9A and 9B illustrate different examples of implementation of the curvature controller 60 which comprises multiple of micro transducers 70 that are connected via wires to an external unit. FIG. 9A illustrates the curvature controller 60 being applied into an inner guiding section 90 of the electrode array 2. FIG. 9B illustrates an example where the curvature controller 60 is pulled out from the inner guiding section 90 when the electrode array 2 is in place within the cochlea.

Figure 10A:
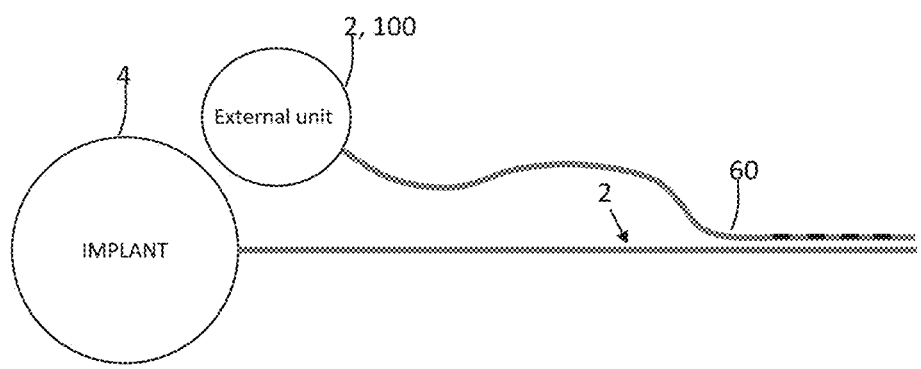
FIGS. 10A and 10B illustrate examples of a curvature controller.
Figure 10B:

FIGS. 10A and 10B illustrate examples on ow the curvature controller 68 is electrical connected to either the implantable receiving unit 4 or an external unit (2,100). In one example, the external unit 100 is a computer that is used by a surgeon for controlling the curvature of the electrode array 2. In another example, the external unit 3 is a sound processor which at least includes a microphone 5. In FIG. 10A, the curvature controller 60 is connected to the external unit (2,100), and in FIG. 10B, the curvature controller 60 is connected to the implantable receiving unit 4.

Figure 11A:
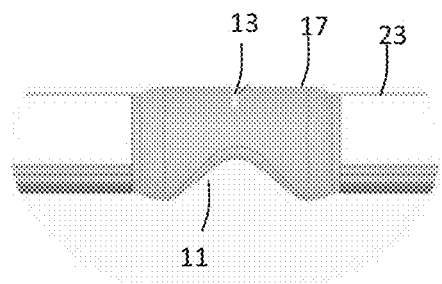
FIGS. 11A and 11B illustrate examples of a silicone notch carrier.
Figure 11B:
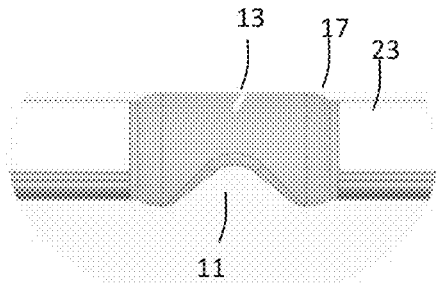

FIGS. 11A and 11B illustrate an example where a slit 13 is formed into a second surface 17 of the silicone notch carrier 11 being opposite to the first surface 16. The second surface 17 is directed away from the spiral ganglion of the cochlea when the electrode array 2 is inserted into the cochlea. By applying the slit the flexibility of the electrode array 2 is even more improved. FIG. 11A illustrates a straight slit 13, and FIG. 11B illustrates an angled slit 13. Not illustrated, an angle of the slit of each silicone notch carrier may vary according to a slit profile and/or the depth of the slit of each silicone notch carrier may vary according to the slit profile.

As used, the singular forms "a," "an," and "the" are intended to include the plural forms as well (i.e. to have the meaning "at least one"), unless expressly stated otherwise. It will be further understood that the terms "includes," "comprises," "including," and/or "comprising," when used in this specification, specify the presence of stated features, integers, steps, operations, elements, and/or components, but do not preclude the presence or addition of one or more other features, integers, steps, operations, elements, components, and/or groups thereof. It will also be understood that when an element is referred to as being "connected" or "coupled" to another element, it can be directly connected or coupled to the other element, but an intervening element may also be present, unless expressly stated otherwise. Furthermore, "connected" or "Coupled" as used herein may include wirelessly connected or coupled. As used herein, the term "and/or" includes all combinations of one or more of the associated listed items. The steps of any disclosed method are not limited to the exact order stated herein, unless expressly stated otherwise.

It should be appreciated that reference throughout this specification to "one embodiment" or "an embodiment" or "an aspect" or features included as "may" means that a particular feature, structure or characteristic described in connection with the embodiment is included in at least one embodiment of the disclosure. Furthermore, the features, structures or characteristics may be combined as suitable in one or more embodiments of the disclosure. The previous description is provided to enable any person skilled in the art to practice the various aspects described herein. Various modifications to these aspects will be readily apparent to those skilled in the art, and the generic principles defined herein may be applied to other aspects. Reference to an element in the singular is not intended to mean "one and only one" unless specifically so stated, but rather "one or more." Unless specifically stated otherwise, the term "some" refers to one or more.

Accordingly, the scope should be judged in terms of the claims that follow.

The invention claimed is:

1. A cochlear implant device comprising:
 an implantable coil configured to receive a plurality of electric stimulation pulses via a transcutaneous link,
 an electrode array including a plurality of electrodes configured to stimulate auditory nerve fibers of a cochlea of a recipient based on the plurality of electric stimulation pulses, and wherein the electrode array comprises:
   a first region including a first group of electrodes of the plurality of electrodes at a basal portion of the electrode array,
   a second region including a second group of electrodes of the plurality of electrodes at an apical portion of the electrode array, where silicone notch carriers are arranged on the electrode array such that one of the silicone notch carriers is arranged between each adjacent pair of the electrodes of the second group, and where each of the silicone notch carriers includes a notch which is formed into the electrode array at the corresponding silicone notch carrier, and when the electrode array is straightened each of the notches has an opening angle which varies between the respective notches of the silicone notch carriers such that the opening angle of the most apical notch has a largest opening angle among the notches of the silicone notch carriers.

2. A cochlear implant device according to claim 1, wherein the first region includes the first group of electrodes of the plurality of electrodes, and where additional silicone notch carriers are respectively arranged on the electrode array between adjacent pairs of the electrodes of the first group, wherein each of the additional silicone notch carriers includes a notch formed into the electrode array at the corresponding additional silicone notch carrier, and when the electrode array is straightened each of the notches of the additional silicone notch carriers has an opening angle which varies between the respective notches of the additional silicone notch carriers.

3. A cochlear implant device according to claim 1, where the opening angle of the at least two or more notches in the second region varies between the notches of the silicone notch carriers according to a dimension profile.

4. A cochlear implant device according to claim 3, wherein the dimension profile includes at least one of following profiles or a combination of following profiles:
the opening angle decreases from a most apical electrode of the second group of electrodes to a first electrode of the second group of electrodes;
the opening angle decreases from a most apical electrode of the second group of electrodes to a most basal electrode of the second group of electrodes;
the bending radius increases from a most apical electrode of the second group of electrodes to a first electrode of the second group of electrodes; and/or
the bending radius increases from a most apical electrode of the second group of electrodes to a most basal electrode of the second group of electrodes.

5. A cochlear implant device according to claim 1, wherein each of the at least two or more notches are formed into a first surface of the silicone notch carrier, where the first surface is directed towards the spiral ganglion of the cochlea when the electrode array is inserted into the cochlea.

6. A cochlear implant device according to claim 1, where a hypothetical center line bisecting the opening angle into two equal segments is symmetrically or asymmetrically arranged according to a center of the silicone notch carrier.

7. A cochlear implant device according to claim 6, wherein the hypothetical center line bisecting the opening angle of at least a silicone notch carrier between a most apical electrode of the second group of electrodes and a first electrode of the second group of electrodes is asymmetrically arranged.

8. A cochlear implant device according to claim 1, wherein the notches shape an open volume which does not include the material of the silicone notch carrier.

9. A cochlear implant device according to claim 1, wherein one or more of the silicone notch carriers include a curvature controller, or a curvature controller is applied onto the one or more silicone notch carriers, and wherein the curvature controller is configured to control the size of the opening angle and/or a bending radius of the notch.

10. A cochlear implant device according to claim 9, wherein the curvature controller includes a micro transducer which is connected to at least one electrode of the second group of electrodes, and wherein the curvature controller is configured to adapt the size of the opening angle of the notch in accordance with an adaptation in an electrical signal applied by the at least one electrode.

11. A cochlear implant device according to claim 9, wherein the micro transducer includes multiple layers of an electro active polymer which are configured to collapse an opening of the notch.

12. A cochlear implant device according to claim 1, wherein the bending radius varies at least between 1.5 mm and 3.25 mm.

13. A cochlear implant device according to claim 5, wherein a slit is formed into a second surface of the silicone notch carrier being opposite to the first surface, where the second surface is directed away from the spiral ganglion of the cochlea when the electrode array is inserted into the cochlea.

14. A cochlear implant device according to claim 13, wherein the slit has a longitudinal axis and the electrode array has a longitudinal axis, and where an angle is formed between the longitudinal axis of the slit and the electrode array, and the slit has a depth along the longitudinal axis of the slit.

15. A cochlear implant device according to claim 14, where the angle is between 25° and 90°.

16. A cochlear implant device according to claim 14, where when the electrode array is straightened, the angle of the slit of each silicone notch carrier varies according to a slit profile and/or the depth of the slit of each silicone notch carrier varies according to a slit profile.

17. A cochlear implant device according to claim 16, wherein the slit profile includes at least one of following profiles or a combination of following profiles:
the slit angle decreases from a most apical electrode of the second group of electrodes to a first electrode of the second group of electrodes;
the slit angle decreases from a most apical electrode of the second group of electrodes to a most basal electrode of the second group of electrodes;
the slit depth decreases from a most apical electrode of the second group of electrodes to a first electrode of the second group of electrodes; and/or
the slit depth decreases from a most apical electrode of the second group of electrodes to a most basal electrode of the second group of electrodes.

18. A cochlear implant device according to claim 2, where the opening angle of the at least two or more notches in the second region varies between the notches of the silicone notch carriers according to a dimension profile.

19. A cochlear implant device according to claim 2, wherein each of the at least two or more notches are formed into a first surface of the silicone notch carrier, where the first surface is directed towards the spiral ganglion of the cochlea when the electrode array is inserted into the cochlea.

20. A cochlear implant device according to claim 3, wherein each of the at least two or more notches are formed into a first surface of the silicone notch carrier, where the first surface is directed towards the spiral ganglion of the cochlea when the electrode array is inserted into the cochlea.

* * * * *